United States Patent [19]

Savard et al.

[11] Patent Number: 5,311,873
[45] Date of Patent: May 17, 1994

[54] COMPARATIVE ANALYSIS OF BODY SURFACE POTENTIAL DISTRIBUTION DURING CARDIAC PACING

[75] Inventors: Pierre Savard, Sainte-Thérèse; Reginald Nadeau, Outremont; Marc Dubuc, Longueuil, all of Canada

[73] Assignee: Ecole Polytechnique, Montreal, Canada

[21] Appl. No.: 937,487

[22] Filed: Aug. 28, 1992

[51] Int. Cl.$^5$ .............................................. A61N 1/00
[52] U.S. Cl. .................................... 128/696; 128/898
[58] Field of Search .................... 128/696, 419 P, 697, 128/786, 419 PT, 898

[56] References Cited

U.S. PATENT DOCUMENTS

| | | | |
|---|---|---|---|
| 4,641,649 | 2/1987 | Walinsky et al. | 128/642 |
| 4,742,831 | 10/1988 | Silvian | 128/696 |
| 4,751,931 | 6/1988 | Briller et al. | 128/700 |
| 4,890,630 | 1/1990 | Kroll et al. | 128/696 |
| 4,940,058 | 7/1990 | Taff et al. | 128/696 |
| 4,974,598 | 12/1990 | John | 128/696 |
| 5,069,215 | 12/1991 | Jadvar et al. | 128/642 |
| 5,083,565 | 1/1992 | Parins | 128/642 |

OTHER PUBLICATIONS

W. M. Jackman et al, "Catheter Ablation of Accessory Atrioventricular Pathways, Wolff-Parkinson-White Syndrome, by Radiofrequency Current", New England Journal of Medicine, 324:1605, 1991.
L. S. Klein et al, "Radiofrequency Catheter Ablation of Ventricular Tachycardia in Patients Without Structural Heart Disease", 85:1666, 1992.
Benson et al, "Localization of the Site of Ventricular Preexcitation with Body Surface Potential Maps in Patients with the Wolff-Parkinson-White Syndrome", Circulation, 65:1259, 1982.
Nadeau et al, "Localization of Preexcitation Sites in the Wolff-Parkinson-White Syndrome by Body Surface Potential Mapping and a Single Moving Dipole Representation", In Electrocardiographic Body Surface Potential Mapping Eds R. T. van Dam, A. van Costerom, Martinus Nijhoff, pp. 95-98, 1986).
Sippens-Groenewegen et al, "Body Surface Mapping of Ectopic Left and Right Ventricular Activation, ORS Spectrum in Patients without Structural Heart Disease", Circulation, 82:879, 1990.
Josephson et al, "Ventricular Activation During Ventricular Endocardial Pacing. II. Role of Pace Mapping to Localize Origin of Ventricular Tachycardia", Am J Cardiol 50:11, 1982.

Primary Examiner—William E. Kamm
Assistant Examiner—Scott M. Getzow
Attorney, Agent, or Firm—Fishman, Dionne & Cantor

[57] ABSTRACT

Body surface potential map (BSPM) pace-mapping is a system and method that can be used in medicine to localize with precision the site of origin of abnormal cardiac electrical activity and to guide the positioning of a catheter over this site of origin, such as the site of ventricular preexcitation in patients with the Wolff-Parkinson-White syndrome or the focus of ectopic activity in patients with tachycardia. Body surface potential distributions are measured with a large number of electrodes, e.g. 24 to 128, distributed over the entire torso surface. The electrical signals are first amplified, converted into digital data and treated to remove electrical or muscle artifacts. Data recorded during abnormal activation (reference beat) are aligned with data recorded during cardiac pacing (paced beat) so as to maximize the average value of the correlation coefficient between the reference and the paced potential distributions during a preset time interval following the beginning of the QRS complex. Reference and paced maps showing color-coded isopotential contour lines are displayed side by side for the same time instant. Visual analysis of these maps according to previously published criteria determines the relative position of the pacing catheter with respect to the focus of abnormal activation, and gives information so as to guide the catheter toward the focus.

21 Claims, 8 Drawing Sheets

COMPARATIVE ANALYSIS OF BODY SURFACE POTENTIAL DISTRIBUTION DURING CARDIAC PACING

BACKGROUND OF THE INVENTION

1. Field of the Invention

The present invention relates to medical instruments and the field of cardiac electrophysiology, and more particularly to the localization of foci of abnormal cardiac activation by comparative analysis of body surface potential distributions during cardiac pacing.

2. Description of the Related Art

The contraction of the human heart is triggered by an electrical process known as an "action potential" which depolarizes the transmembrane potential of the myocardial cells. This depolarization process is automatic (i.e. an isolated cardiac cell can show repeated action potentials) and also, it propagates from one cell to the neighboring cells. In the normal heart, activation originates from the cells having the fastest ation potential frequency which are located in the sino-atrial (SA) node. The activation propagates from the SA node to the rest of the atria, and then to the ventricles through the atrio-ventricular (AV) node, which slows down propagation so as to permit the flow of blood from the atria to the ventricles, and then through the His bundle and the Purkinje conduction system which synchronizes the ventricular activation.

Congenital heart diseases or complications following coronary artery disease can produce an abnormal increase of the heart rate known as tachycardia which can be potentially lethal. In patients with the Wolff-Parkinson-White (WPW) syndrome (a congenital disease), an additional conduction pathway joins the atria and the ventricles and this accessory AV pathway can either be responsible for the continuous activation of the ventricles during atrial tachyarrhythmias, or create a reentrant circuit in which activation propagates repeatedly through the ventricles, the accessory AV pathway, the atria, the AV node and the ventricles again. In patients with idiopathic ventricular tachycardia or in patients with ventricular tachycardia (VT) resulting from myocardial infarction, the abnormal activation originates during VT from a circumscribed region of the ventricles with abnormal automaticity and/or propagation properties.

These disorders of the heart rhythm may be cured by the catheter ablation of the arrhythmogenic sites, either the accessory AV pathways or the sites of origin of VT. See: W. M. Jackman et al., "Catheter ablation of accessory atrioventricular pathways, Wolff-Parkinson-White syndrome, by radiofrequency current", New Engl J Med 324:1605, 1991; L. S. Klein et al., "Radiofrequency catheter ablation of ventricular tachycardia in patients without structural heart disease", Circulation 85:1666, 1992. Catheter ablation consists of inserting a catheter percutaneously through veins or arteries inside the heart cavities. The tip of the catheter is placed near the arrhythmogenic site. Electromagnetic energy is then delivered to the myocardium by electrodes or antennas located at the catheter tip. Electromagnetic energy can be used within a wide frequency spectrum ranging from DC current to radiofrequency current, microwave and laser light. The effects of this localized energy delivery is to destroy the arrhythmogenic site and to create a small permanent lesion.

One of the problems with the catheter ablation of arrhythmogenic sites is the duration of the procedure. This procedure is long because cardiologists rely on electrograms recorded with electrodes located near the catheter tip to guide the positioning of the catheter within millimeters of the arrhythmogenic site. On these electrograms, the timing of the local activation deflexion or the presence of accessory pathway potentials can only indicate if the catheter tip is near or far from the arrhythmogenic site, and if it is far, it does not indicate in which direction to move the catheter.

Information about the location of the arrhythmogenic site can be obtained from body surface potential maps (BSPM). As ventricular activation progresses away from the accessory AV pathway or from the VT site of origin, the activation currents generate electrical potentials that can be measured over the torso surface by a large number of electrodes. For WPW patients, Benson et al. (Benson et al., "Localization of the site of ventricular preexcitation with body surface potential maps in patients with the Wolff-Parkinson-White syndrome", Circulation, 65:1259, 1982) correlated the patterns of BSPM recorded during the preexcitation of the ventricles through the accessory AV pathway (delta wave) with the preexcitation sites determined by electrophysiologic studies or surgical ablations and they concluded that at least seven preexcitation sites could be predicted by analysis of the BSPM patterns. Similar patterns were reported by Nadeau et al. (Nadeau et al. "Localization of preexcitation sites in the Wolff-Parkinson-White syndrome by body surface potential mapping and a single moving dipole representation". In Electrocardiographic body surface potential mapping Eds R. T. van Dam, A. van Oosterom, Martinus Nijhoff, pp: 95–98, 1986) in patients who underwent arrhythmia surgery and/or an electrophysiologic study. The latter also noted the progressive changes in the morphology of the BSPM recorded during the delta wave in patients with adjacent preexcitation sites, thus reflecting the continuous distribution of possible accessory AV pathways around the AV ring with the position of the minimum and of negative potentials on the BSPM identifying the pathway location: prominent negativity on the right side of the anterior torso correspond to patients with preexcitation sites located in the right ventricle; a minimum on the back correspond to sites in the left ventricle; negativity over the entire lower torso correspond to posteroseptal sites; otherwise, positivity over the entire lower torso correspond to anterior sites. Similarly, for the localization of sites of origin of VT, Sippens-Groenewegen et al. (Sippens-Groenewegen et al., "Body surface mapping of ectopic left and right ventricular activation. QRS spectrum in patients without structural heart disease", Circulation, 82:879, 1990) reported BSPM patterns obtained during ventricular pacing at known sites and which can be used to estimate the site of origin of ectopic activity.

Another approach to the localization of abnormal cardiac activation which uses electrocardiographic potentials consists of comparing the standard twelve-lead electrocardiogram (ECG) during ventricular pacing at different sites, with the ECG recorded during abnormal ventricular activation (pacing consists of initiating the activation process of the ventricles by applying a small current pulse between the electrodes of a catheter located inside the ventricles). This "pace-mapping" approach relies on the visual analysis of twelve time-varying signals. It can confirm that the pacing catheter is located over the focus of abnormal activation when the paced ECG and the abnormal ECG are identical (because the cardiac activation that generates these two ECGs are localized at the same site). However, it gives only limited information about which direction to move the catheter toward the focus when the two ECG are not identical. See: Josephson et al., "Ventricular activation during ventricular endocardial pacing. II. Role of pace mapping to localize origin of ventricular tachycardia", Am J Cardiol 50:11, 1982.

The Patent literature also provides teachings which are of interest having regards to the invention as described and claimed in the following, for example, U.S. Pat. No. 4,974,598, John, Dec. 4, 1990, U.S. Pat. No. 5,083,565, Parins, Jan. 28, 1992, U.S. Pat. No. 5,069,215, Jadvar et al, Dec. 3, 1991, U.S. Pat. No. 4,751,931, Briller et al, Jun. 21, 1988 and U.S. Pat. No. 4,641,649, Walinsky et al, Feb. 10, 1987.

The teachings of the '598 patent relate to early detection of heart disease with an EKG system which detects heart beats having P, Q, R, S, T and U portions. A large number of electrodes (32 to 64) are placed on the torso of the patient. Readings taken are subjected to statistical analysis and compared with readings of a normal population.

In the '565 patent, an electrosurgical catheter includes a sensor for sensing the polarization signals developed in the heart and for transmitting the sensed signals to an external EKG monitor. It also includes insulated tips to which an RF signal may be applied to destroy selected cells.

A disposable esophageal electrode structure, as taught in the '215 patent, includes a plurality of spaced apart conductive electrode members. Each electrode is connected to a wire by which it is connected to external electrical units.

In the '931 patent, surface electrodes are positioned on the surface of the patient's body in the heart area of the patient. Surface ECG's acquired are enhanced by filtering and then subjected to method steps for detecting low level bioelectric signals.

The '649 patent teaches a method for selective ablation of cardiac tissues by high frequency electromagnetic energy. A catheter, which is introduced into a patient's heart chamber, is terminated by an antenna. Depolarization signals are coupled by the antenna to an ECG monitor for display. External electrodes also detect potentials which are displayed on the monitor. Accordingly, the position of the antenna is adjusted to an appropriate position for ablation procedures.

OBJECTIVES AND SUMMARY OF THE INVENTION

So as to decrease the duration of catheter ablation of arrhythmogenic sites, we have invented a method and apparatus that gives useful information about the location of the ablation catheter with respect to the arrhythmogenic site. The present method and apparatus is called body surface potential map (BSPM) pace-mapping. It constitutes a significant improvement of two previously known techniques: body surface potential mapping and pace-mapping. For WPW patients, the ease of interpretation of the BSPM patterns and the progressive changes observed for adjacent preexcitation sites constitute the basis of BSPM pace-mapping to guide the catheter ablation of accessory AV pathways. The first step of this method is to position the catheter at the preexcitation location predicted by the BSPM recorded during the delta wave for a sinus rhythm beat. Then, the ventricles are paced with this catheter and the BSPMs recorded during the paced QRS are compared with the preexcited BSPM: this visual comparison indicates if the pacing site is too anterior or posterior with respect to the preexcitation site, and the catheter is moved accordingly. This process is repeated until the preexcited and paced BSPM patterns are identical, then ablation may be attempted.

The body surface potentials are measured with a large number (e.g. 24 to 128) of electrodes distributed over the front, sides and back of the torso. The electric signals from the electrodes are amplified, filtered, digitized and stored on a magnetic disk. During data acquisition, a reference signal from one of the ECG leads is constantly displayed on a terminal to allow the manual selection of a one second window containing the beat to be analyzed.

The first step of the computerized BSPM analysis consists of the automatic identification and correction of faulty leads. Thus, signals that are saturated as well as signals contaminated by excessive electrical noise are considered faulty and are replaced by interpolating the signals from the nearest valid leads. Then, the onset of the QRS complex is automatically detected. For each lead, the value of the potential at the QRS onset is subtracted from all samples so as to correct any baseline shift.

Data recorded during abnormal activation (reference beat) are aligned with data recorded during cardiac pacing (paced beat) so as to maximize the average value of the correlation coefficient between the reference and the paced potential distributions during a preset time interval (typically 40 msec) following the beginning of the QRS complex. Reference and paced BSPMs with color-coded isopotential contour lines are then shown side by side on a video terminal for the time instant having the highest correlation coefficient during the preset time interval. Similar pair of maps can be rapidly displayed for all successive time instants as in an animated movie. As an aid for the visual comparison of the paced and reference BSPMs, a paced map showing only the zero isopotential contour line and the locations of the maximum and minimum potential values is superimposed exactly over the reference map which has the same format but a different color. So as to assess quantitatively the similitude between the reference and paced BSPMs, the correlation coefficient between the reference and paced body surface potential distributions is plotted for all sampling instants during the preset time interval.

In accordance with a particular embodiment of the invention there is provided a method of locating a position of interest in the heart of a patient and in positioning a surgical instrument at this position, comprising the steps of:

A. placing a plurality of electrodes on the surface of said patient in the area of the torso of the patient;

B. obtaining readouts from said electrodes during a pre-excitation phase or at the onset of an abnormal beat and forming therefrom a first body surface potential map (BSPM);

C. estimating said position of interest from said first BSPM;

D. placing said surgical instrument at said estimated position;

E. pacing the heart of said patient with an electrical signal applied through said surgical instrument;

F. obtaining readouts from said electrodes during said paced phase and forming a further BSPM therefrom;

G. determining from said further BSPM, when compared with the first BSPM, if the surgical instrument is in the correct position;

H. if the instrument is not in the correct position, moving the instrument in a direction as indicated by the comparison of the further BSPM with the first BSPM;

I. repeating steps E. to G. until the surgical instrument is at the position of interest.

BRIEF DESCRIPTION OF THE DRAWINGS

The invention will be better understood by an examination of the following description, together with the accompanying drawings, in which.

DETAILED DESCRIPTION OF THE INVENTION

1. Introduction and Method Overview

Some types of potentially lethal arrhythmias may be cured by the catheter ablation of the arrhythmogenic sites. These sites can be an accessory AV pathway in patients with the WPW syndrome, or the site of origin of VT in patients with prior myocardial infarction or idiopathic VT. Catheter ablation is a long procedure because it is guided by electrograms recorded from the catheter which give limited information about the relative distance between the catheter and the arrhythmogenic site. So as to decrease the duration of catheter ablation procedure, we have invented a method and apparatus that gives useful information about the location of the ablation catheter with respect to the arrhythmogenic site. This approach relies on the analysis of electrical potentials measured over the entire torso surface and which are produced by cardiac activation in the vicinity of the arrhythmogenic site. The present method and apparatus is called: body surface potential map (BSPM) pace-mapping.

Figure 1C:
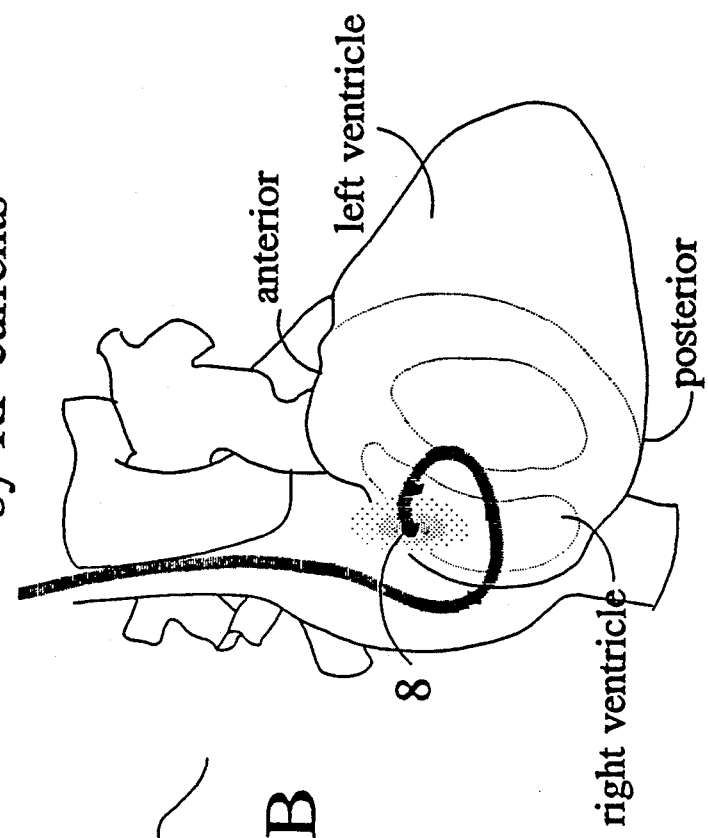
FIG. 1C illustrates the catheter ablation of the accessory AV pathway.
Figure 1B:
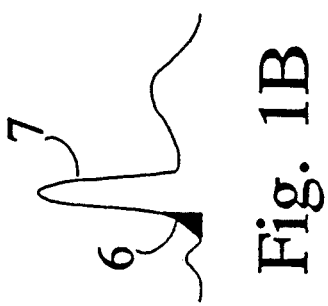
FIG. 1B illustrates the ECG produced by the ventricular preexcitation.
Figure 1A:
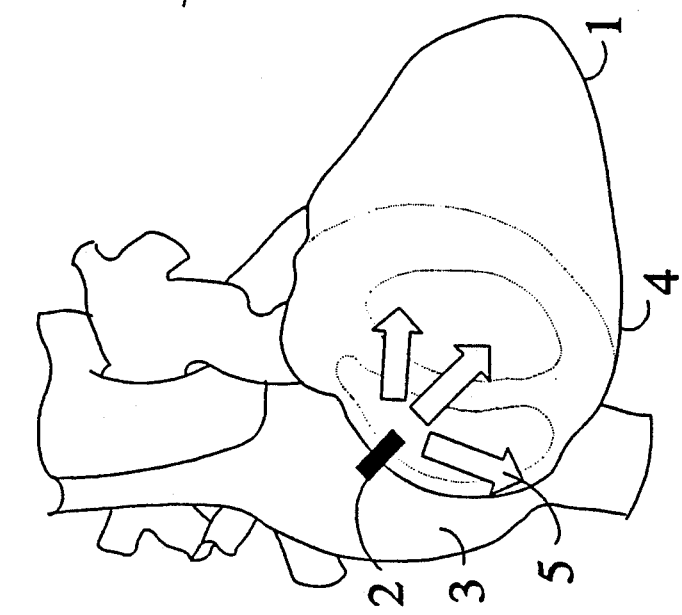
FIG. 1A is a diagram of the heart of a WPW patient.

FIG. 1A illustrates the heart 1 of a WPW patient with an accessory pathway (AP) 2 joining the atria 3 and the ventricles 4. During normal sinus rhythm, activation propagates through this pathway and activates the ventricles before normal activation from the AV node has had time to reach the ventricles. This local "preexcitation" 5 of the ventricles generates electrical potentials on the body surface that are known as the "delta wave" 6 (FIG. 1B) and which precedes, on the electrocardiogram, the QRS complex 7 which is generated by the activation of the ventricles. FIG. 1C illustrates the catheter ablation of the accessory AV pathway by radiofrequency currents (500 KHz) injected through the catheter tip 8. The high current density near the catheter tip increases the myocardial temperature and creates a small lesion that destroys the accessory pathway. For WPW patients, BSPM pace-mapping relies on the potential distributions measured over the entire torso surface during the delta wave and which are used as reference maps. For patients with ventricular tachycardia BSPM recorded after the QRS onset are used as reference maps.

Figure 2:
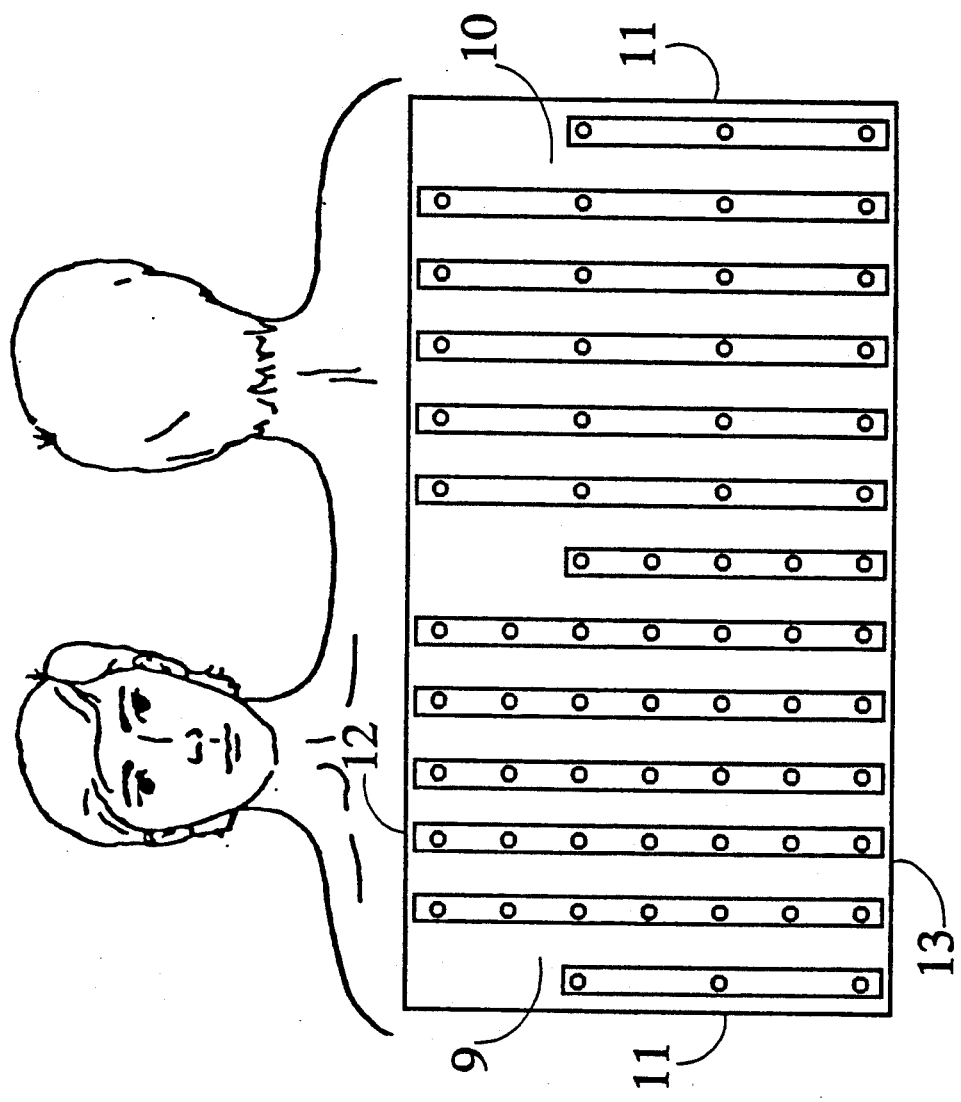
FIG. 2 shows the electrode strips over the torso and the rectangular map format of the BSPMs.

FIG. 2 illustrates a typical electrode arrangement for the recording of the electrocardiographic potentials over the front, sides and back of the torso. FIG. 2 also illustrates the rectangular format of the BSPMs: the left part of the map corresponds to the anterior chest 9; the right part, to the posterior chest 10; both sides of the map correspond to the right mid-axillary line 11; the top, to the suprasternal notch 12; and the bottom, to the waist 13. On the BSPMs, isopotential lines join points with the same potential value, the zero potential line is identified by a heavier line and the plus and minus signs identify the locations of the potential maximum and minimum (see FIGS. 3A to 3C).

Figures 3A, 3B, 3C:
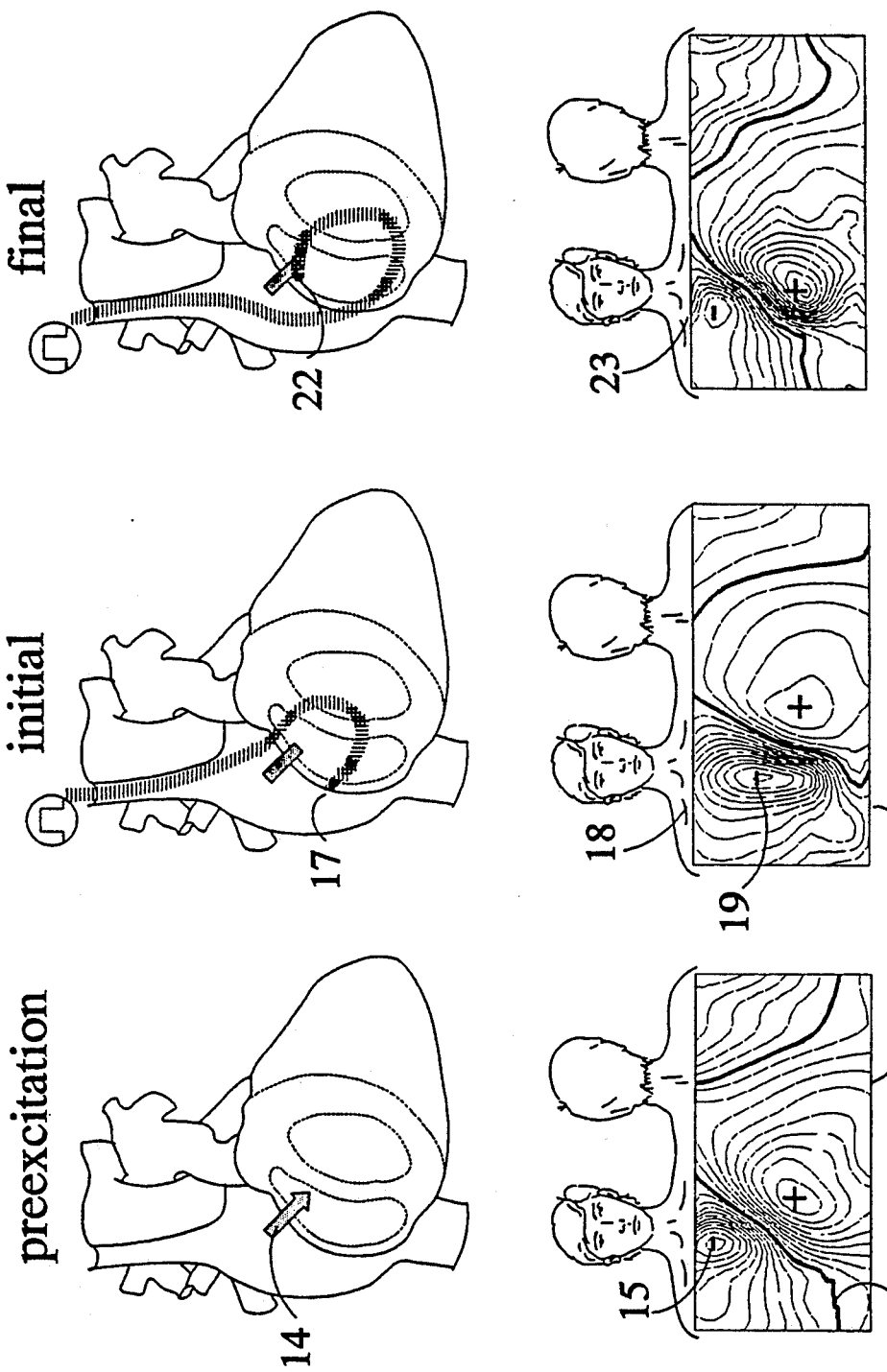
FIGS. 3A to 3C show successive steps of the SPM pace-mapping method.

FIGS. 3A to 3C show examples of the application of the BSPM pace-mapping method for a WPW patient with a right-sided accessory pathway 14. The on-line analysis of the BSPM recorded during the delta wave at the beginning of the investigation (FIG. 3A) indicated a right anterior ventricular preexcitation site according to the criteria presented in the Description of the Related Art: the potential minimum 15 is on the right side of the torso and negativity does not extend to the lower torso 16. The ablation catheter 17 was then positioned approximately at that site and the ventricles were paced. BSPMs 18 recorded during the paced QRS complex (FIG. 3B) are not identical to the preexcited BSPMs: the location of the minimum 19 is lower than on the preexcited BSPMs and negativity 20 extends to the lower torso, whereas the lower torso 21 was positive on the preexcited BSPM. According to same criteria, this first pacing site was estimated to be not anterior enough and the ablation catheter was moved to a more anterior site 22 (see FIG. 3C). For the BSPMs 23 recorded during ventricular pacing at this second site (FIG. 3C), the locations of the BSPM extrema and the BSPM morphology were visually identical to the preexcited BSPM and the correlation coefficient was higher than for the first pacing site (0.92 vs 0.88).

BSPM pace-mapping constitutes a significant improvement of two previously known techniques: body surface potential mapping and pace-mapping. Compared to the body surface potential mapping of the abnormal potential distributions, BSPM pace-mapping: 1) provides additional information about the location of the ablation catheter with respect to the focus of abnormal activation; 2) is a self-correcting procedure that reduces the importance of BSPM differences that are not specific to the location of the focus of abnormal activation, such as those due to individual differences in the size and shape of the torso or heart, for example, a patient with a preexcited BSPM suggestive of a right lateral accessory pathway and who was paced at that site showed a right anterior pattern on the paced BSPMs, the pacing catheter was thus moved inferiorly and the preexcitation site was finally localized in the posteroseptal region. Also, compared to the standard pace-mapping technique which utilizes the twelve lead ECG, BSPM-pace mapping: 1) provides much more information about the spatial distribution of the body surface potentials than the twelve lead ECG, specially in the back and on the right side of the torso; 2) significant electrocardiographi8c differences between adjacent pacing sites are more easily perceived by comparing maps than twelve ECG tracings. The following sections describe the apparatus necessary for the comparison of the reference BSPM and the paced BSPM.

2. Data Acquisition and Pre-processing

The body surface potentials are measured with a large number (e.g. 24 to 128) of unipolar leads referenced to the Wilson Central Terminal (WCT). The electrodes are located over the front, sides and back of the torso. There should be at least 8 electrodes on the back. Preferably, the electrodes are radiotransluscent so as to prevent interference on the fluoroscopic images during the electrophysiologic study and the ablation procedure. The electrodes can be mounted on vertical adhesive strips for rapid positioning over the torso surface (FIG. 2).

Figure 4:
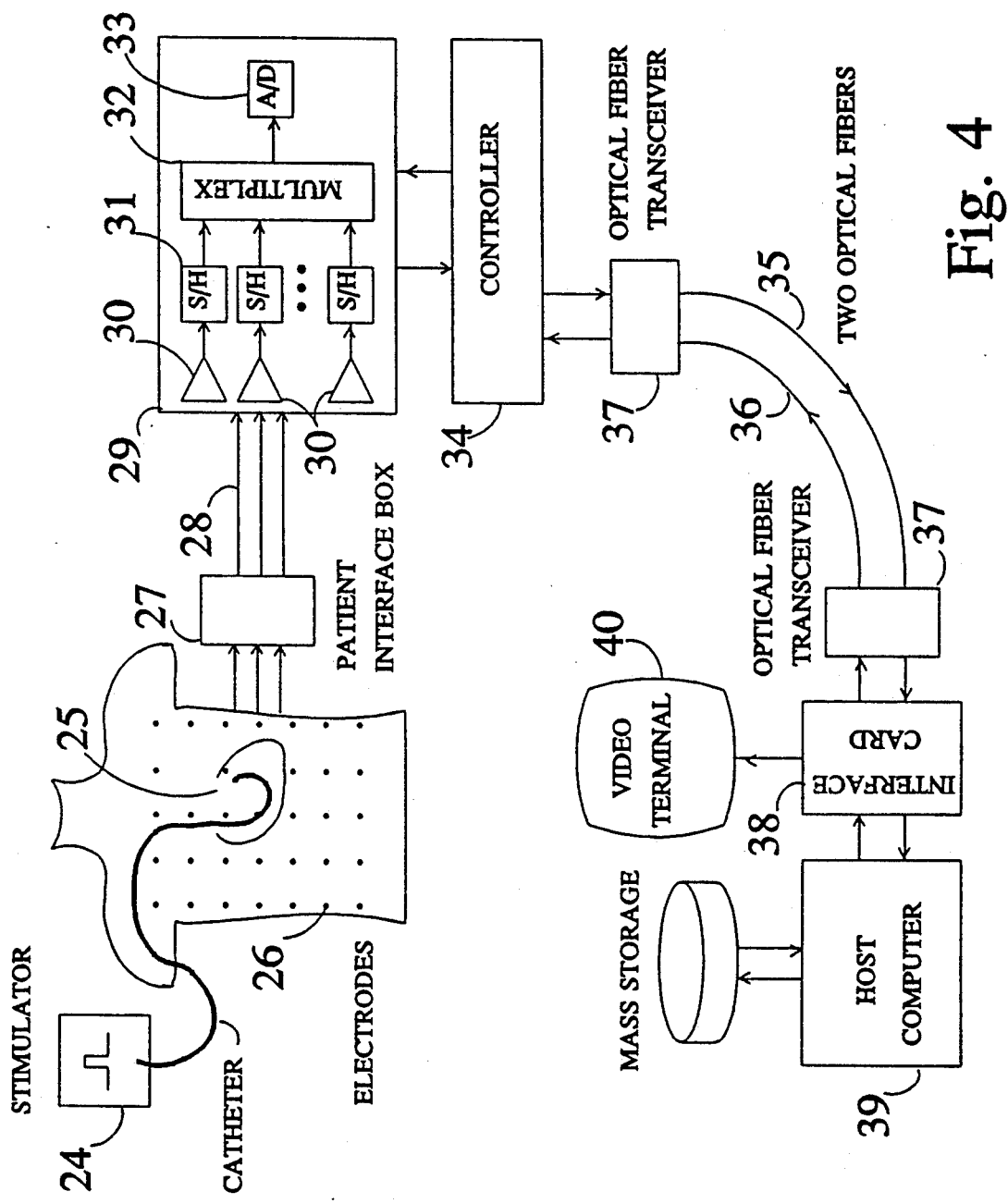
FIG. 4 is a block diagram of the preferred embodiment of the data acquisition system.

FIG. 4 shows the block diagram of the preferred embodiment of the data acquisition system. This figure also shows the stimulator 24 which is used to deliver a short current pulse through electrodes located at the extremity of a catheter inserted in the heart 25 of a patient. The thoracic electrodes 26 described in the preceding paragraph are electrically connected to a patient interface box 27. Inside this box, each thoracic electrode is connected to a surge limiter device so as to protect the amplifiers against any surge voltage (possibly due to a defibrillator) and three signals from electrodes located on both arms and the left leg are electrically summated so as to serve as the electrical reference (the WCT). A patient cable 28 joins the patient interface box to the data acquisition unit 29, transmitting the electrical signals from the thoracic electrodes and the WCT. The potential difference between any thoracic electrode and the WCT is amplified with an amplifier 30 having a programmable gain (40× to 10000×), a programmable high-pass cutoff frequency (0.05 Hz or DC) and a programmable low-pass cutoff frequency (250, 500 or 1000 Hz). Each amplifier is followed by a sample-and-hold circuit 31 so that all channels are sampled simultaneously. For each group of 16 channels, the output of the sample-and-hold amplifier is connected to a multiplexer circuit 32. Then, the output of the multiplexer is connected to a 12 bit analog-to-digital (A/D) converter 33 with a conversion time shorter than 10 microsecond. Sampling frequency is above or equal to 500 samples per second. Amplification, sampling and conversion operations are coordinated by a hardware controller 34. So as to minimize any leakage current to the patient, the data acquisition unit is powered by a low-leakage power supply and it is connected to the host computer by two optical fibers, one (35) for transmitting the data to the computer and the other (36) for transmitting commands (e.g. setting the amplifier gains or the sampling frequency) to the controller. The optical fibers are connected at both ends to optical fiber transceivers 37 which convert the data format from parallel to serial, and transforms electrical signals to optical signals and vice-versa. An interface card 38 connected to the internal BUS of the host computer 39 handles the exchange of data between the data acquisition unit and the host computer as well as the display of results on a color video terminal 40. The host computer has a minimum of 5 Mb of memory and 70 Mb of mass storage space.

Figure 5:
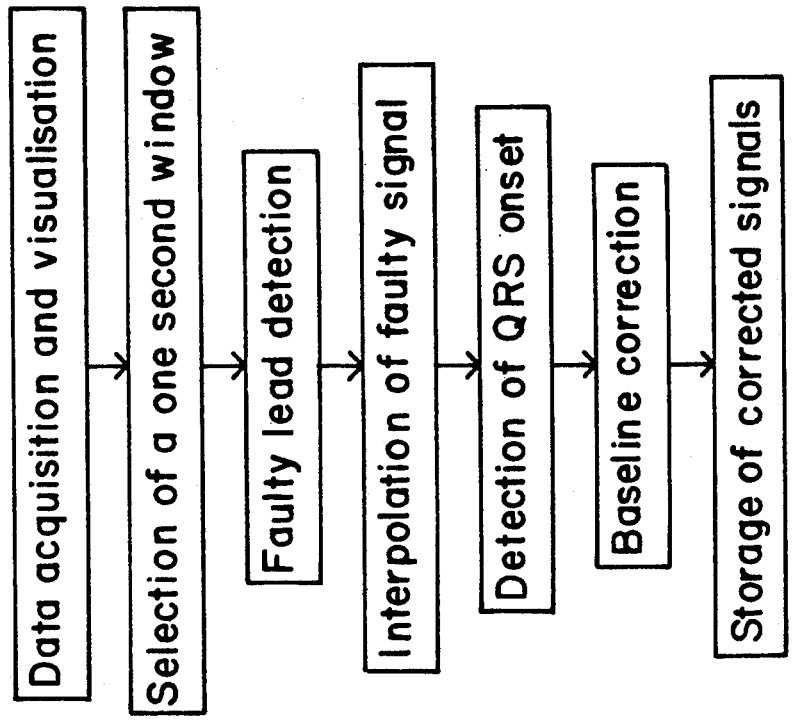
FIG. 5 is a block diagram of the data acquisition and pre-processing.

FIG. 5 shows a flow chart of the data acquisition and pre-processing steps. During data acquisition, the program constantly displays a reference signal from one of the ECG leads on a video terminal to allow the manual selection of a one second window containing the beat to be analyzed. After beat selection, the next step of the pre-processing phase consists of the automatic identification of faulty leads. For each lead, the number of time instants at which the absolute value of the potential exceeds a preset percentage of the dynamic range is first computed (this preset percentage is about 95%), if this number corresponds to a consecutive duration of more than a preset duration (about 50 msec), then the amplifier is considered to be saturated and the lead is considered faulty. Also, for each lead, the signal is filtered with a numerical high-pass filter with a cut-off frequency of about 50 Hz, if the total power of the filtered signal (computed as the sum of the square of each sample of the filtered signal) exceeds a preset threshold, then the lead is considered faulty because it contains an excessive level of electrical noise.

Each of the faulty signals is replaced by linear interpolation using the signals from the neighboring leads. For each valid lead within a preset radius around the faulty lead (this radius is about twice the distance between the electrodes), the potential is divided by the distance which separates it from the faulty lead and summated. The sum is then divided by the sum of the inverse of each of those distances, and assigned to the faulty lead. This procedure is applied for all sampling instants.

The onset of the QRS complex is then automatically detected by using the root-mean-square (RMS) signal computed from a subset of M leads (for each sampling instant, the RMS value corresponds to the square root of the sum of the square of the potential at each lead of the subset divided by the number of leads M). Starting backwards from the time instant having the largest RMS value within the one second analysis window, the first time instant at which the slope of the RMS signal becomes negative while the RMS potential is lower than a preset percentage of the maximum RMS value (about 10%) is selected as the QRS onset.

For each lead, the value of the potential at the QRS onset is subtracted from all samples so as to correct any baseline shift. After the correction of faulty leads and baseline shift and the determination of the QRS onset, the data within the one second analysis window are then stored on magnetic disk.

Figure 6:
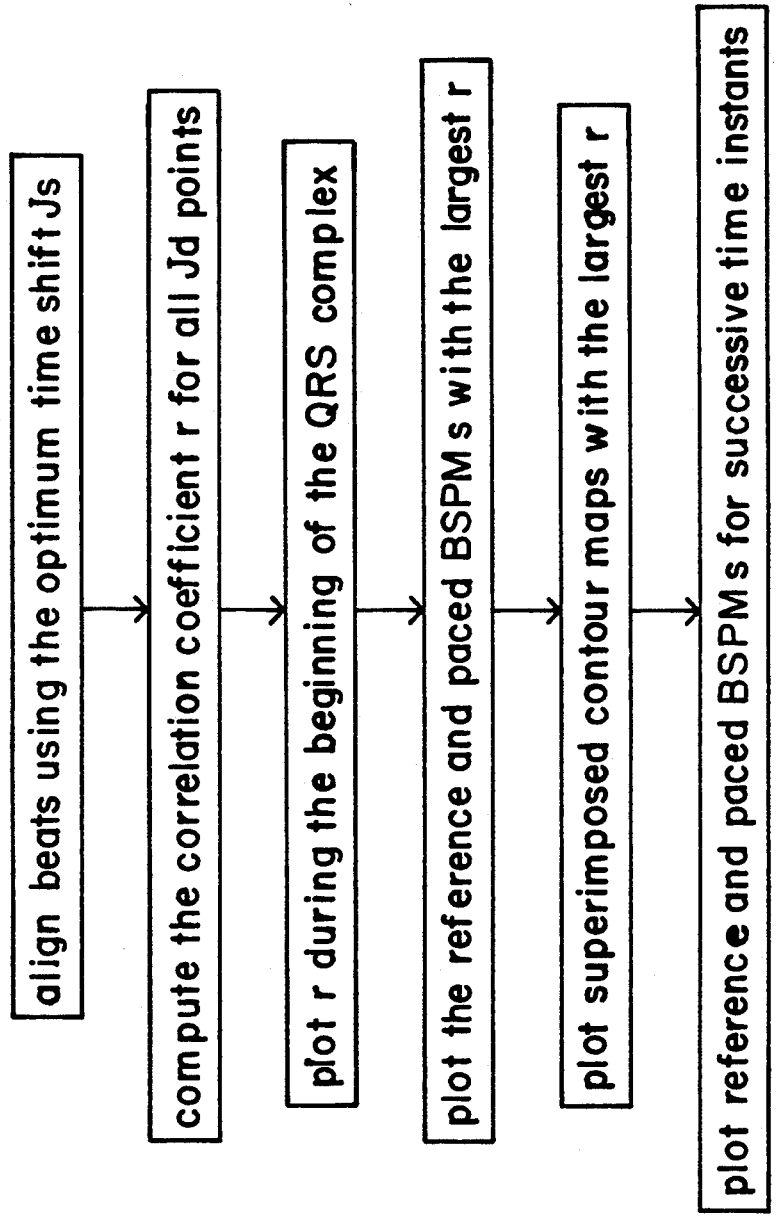
FIG. 6 is a block diagram of the beat alignment and the comparative analysis of the paced and reference BSPM.

3. Beat Alignment and Comparative Analysis of Paced BSPMs and Reference BSPMs Data recorded during abnormal activation (reference beat) are precisely aligned with data recorded during cardiac pacing (paced beat) so as to allow a meaningful comparison between BSPMs recorded at similar time instants after the QRS onset. FIG. 6 is a flow chart of the beat alignment and the comparative analysis steps of the paced and reference BSPM.

Figure 7:
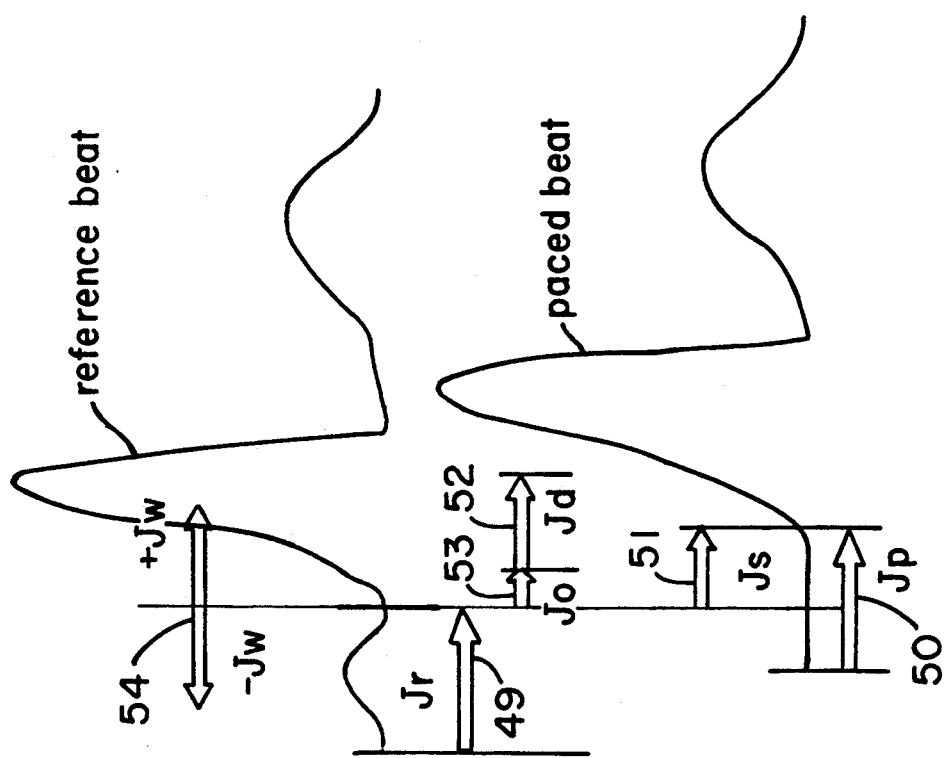
FIG. 7 shows variables used for the alignment of the paced and reference QRS complexes.
Figure 8A:
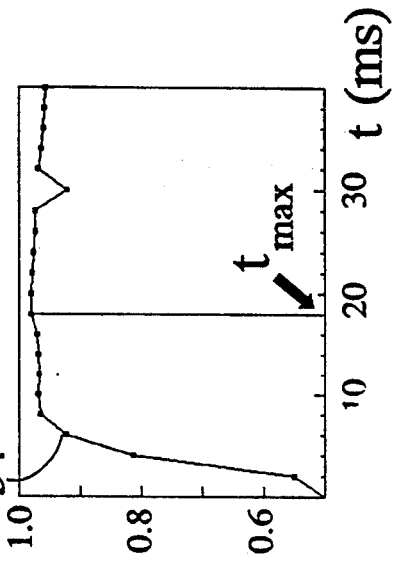
FIGS. 8A to 8D illustrate the comparative display of the reference and paced BSPMs on a video terminal.
Figure 8B:
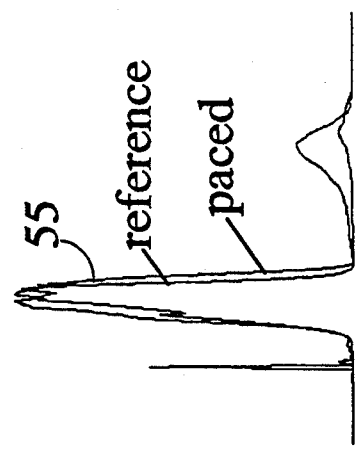
Figure 8D:
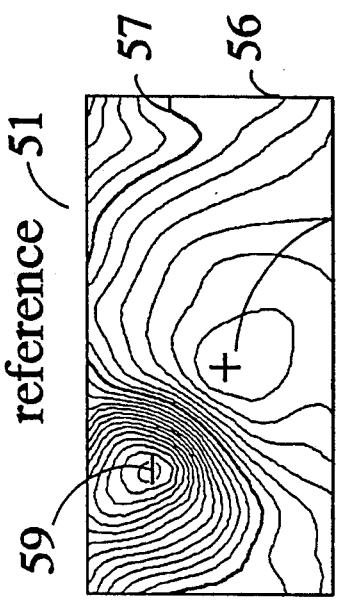
Figure 8C:
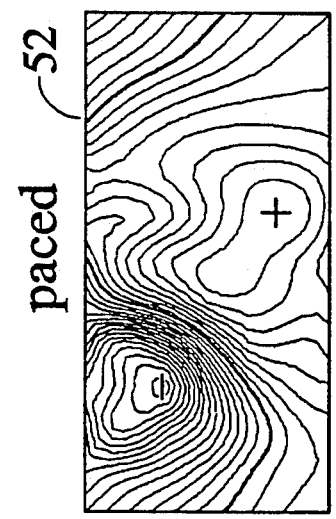

The paced QRS and the reference QRS are automatically aligned so as to maximize the average value of the correlation coefficient between the reference and the paced potential distributions during a preset time interval (typically 40 msec) following the beginning of the QRS complex. This average value of the correlation coefficient is given by:

$$\bar{r} = \frac{N}{Jd} \sum_{J=Jo}^{Jo+Jd} \frac{\sum_{I=1}^{N} (Vr(I,Jr+J) - \bar{Vr}(Jr+J))(Vp(I,Jp+Js+J) - \bar{Vp}(Jp+Js+J))}{\left(\sum_{I=1}^{N}(Vr(I,Jr+J) - \bar{Vr}(Jr+J))^2\right)\left(\sum_{I=1}^{N}(Vp(I,Jp+Js+J) - \bar{Vp}(Jp+Js+J))^2\right)}$$

where N is the number of leads; Vr(I,J) is the potential at lead I and time instant J for the reference beat (the time instant J is measured from the beginning of the reference beat window); Vp(I,J) is the potential at lead I and time instant J for the paced beat (the time instant J is measured from the beginning of the paced beat window); $\bar{V}r(J)$ is the average potential for all N leads at time instant J for the reference beat; $\bar{V}p(J)$ is the average potential for all N leads at time instant J for the paced beat; Jr 49 is the time instant of the beginning of the QRS complex of the reference beat measured from the beginning of the reference beat window; Jp 50 is the time instant of the beginning of the QRS complex of the paced beat measured from the beginning of the paced beat window; Js 51 is the time shift between the paced beat and the reference beat; Jd 52 is the number of time instants following the QRS onset which are used to compute the average value of the correlation coefficient, it corresponds to about 40 msec; Jo 53 is the time instant of the beginning of the QRS onset for both beats after a shift of the paced beat of Js time instants, Jo is equal to=Js/2 (See FIG. 7). Thus, for each value of time shift Js within the range −Jw<Js<+Jw 54, the average value of the correlation coefficient is computed and the time shift corresponding to the maximum value is used to shift the paced beat with respect to the reference beat.

So as to assess quantitatively the similitude between the reference and paced BSPMs, the correlation coefficient between the reference and paced body surface potential distributions is plotted for all sampling instants during the preset time interval Jd (0<J<Jd) according to:

$$r(J) = \frac{N \sum_{I=1}^{N}(Vr(I,Jr+J) - \bar{Vr}(Jr+J))(Vp(I,Jp+Js+J) - \bar{Vp}(Jp+Js+J))}{\left(\sum_{I=1}^{N}(Vr(I,Jr+J) - \bar{Vr}(Jr+J))^2\right)\left(\sum_{I=1}^{N}(Vp(I,Jp+Js+J) - \bar{Vp}(Jp+Js+J))^2\right)}$$

For the time instant having the highest correlation coefficient, reference 51 and paced 52 BSPMs are shown side by side on a video terminal. Also shown are the time course of the correlation coefficient 54 and the superimposed RMS signals for the reference and paced beats 55 (FIG. 8). For the time instant having the highest correlation coefficient, the RMS potential difference between the reference and paced body surface potentials measured on all leads is also computed and displayed. Similar pair of maps can be rapidly displayed for all successive time instants as in an animated movie. On the BSPMs, the torso surface is represented in a rectangular format, the isopotential lines that join points with the same potential value are obtained by cubic spline interpolation 56, isopotential contour lines are color coded, the zero potential line is identified by a heavier line 57, the plus 58 and minus 59 signs identify the locations of the potential maximum and minimum respectively.

As an aid for the visual comparison of the paced and reference BSPMs, a paced map showing only the zero isopotential contour line and the plus and minus signs identifying the thoracic locations of the maximum and minimum potential values can also be shown superimposed exactly over the reference map which has the same format, but a different color.

Although a particular embodiment has been described, this was for the purpose of illustrating, but not limiting, the invention. Various modifications, which will come readily to the mind of one skilled in the art, are within the scope of the invention as defined in the appended claims.

We claim:

1. A method of locating a position of interest in the heart of a patient and in positioning a surgical instrument at this position, comprising the steps of:
   A. placing a plurality of electrodes on the surface of said patient in the area of the torso of the patient;
   B. obtaining readouts from said electrodes during a pre-excitation phase or at the onset of an abnormal beat and forming therefrom a first body surface potential map (BSPM);
   C. estimating said position of interest from said first BSPM;
   D. placing said surgical instrument at said estimated position;
   E. pacing the heart of said patient with an electrical signal applied through said surgical instrument;
   F. obtaining readouts from said electrodes during said paced phase and forming a further BSPM therefrom;
   G. determining from said further BSPM, when compared with the first BSPM, if the surgical instrument is in the correct position;
   H. if the instrument is not in the correct position, moving the instrument in a direction as indicated by the comparison of the further BSPM with the first BSPM;
   I. repeating steps E. to G. until the surgical instrument is at the position of interest.

2. A method as defined in claim 1 wherein said first BSPM is obtained during the delta wave for a sinus rhythm beat in WPW patients or at the beginning of the QRS in patients with ventricular tachycardia.

3. A method as defined in claim 1 wherein said instrument is a catheter and said catheter is inserted into the ventricles of said patient's heart.

4. A method as defined in claim 1 wherein said BSPM's are displayed on a CRT terminal.

5. A method as defined in claim 4 and including the further step of selecting one of said electrodes to provide a reference signal to permit the manual selection of a window containing the beat to be analyzed.

6. A method as defined in claim 1 and including a preliminary step, carried out before step A, of automatically identifying and correcting faulty leads, that is, leads which carry signals which are saturated as well as signals contaminated by excessive electrical noise.

7. A method as defined in claim 6 wherein said preliminary step includes interpolating signals from valid leads near leads which have been identified as faulty.

8. A method as defined in claim 1 wherein, in steps A and F, the onset of a QRS complex is automatically detected and the value of the potential at the QRS onset is subtracted from the read-outs of all leads so as to correct for any baseline shifts.

9. A method as defined in claim 1 wherein the determination as recited in step G is obtained by as formed in step B and the BSPM as formed in step F.

10. A method as defined in claim 9 wherein the data of the read-outs obtained in step B are aligned with the data of the read-outs obtained in step F so as to maximize the average value of said correlation coefficient.

11. A method as defined in claim 10 wherein said data is aligned by analyzing the correlation coefficient during a preset time interval following the beginning of the QRS complex.

12. A method as defined in claim 11 wherein said BSPMs are displayed on a CRT;
and including the further step of displaying the BSPM formed in step B during said preset time interval alongside of the BSPM formed in step F during said preset time interval on said CRT for visual comparison.

13. A method as defined in claim 12 wherein said BSPMs comprise isopotential lines including a zero isopotential line, a maximum potential marker and a minimum potential marker;
and including the further step of displaying only the zero isopotential line and the locations of the maximum and minimum potential values for said BSPMs.

14. A method as defined in claim 13 and including the step of providing a plot of correlation coefficients for predetremined instances during said preset time interval.

15. A method as defined in claim 6 and including the step of selecting a dynamic range of value for the read-outs obtained from said electrodes;
determining the number of time instances at which each read-out exceeds a preset percentage of this dynamic range;
determining if this number of instances corresponds to a consecutive duration greater than a preset duration; and
if said read-out from an electrode exceeds the preset duration, considering that the output of this read-out of this electrode is faulty.

16. A method as defined in claim 15 wherein the preset percentage is 95% and the preset duration is 50 msec.

17. A method as defined in claim 6 and including filtering the read-out of each electrode with a numerical high-pass filter with a cut-off frequency of 50 Hertz and determining if the total power of the filtered signal exceeds a preset threshold; and
if the filtered signal exceeds the preset threshold, considering the read-out of said electrode to be faulty.

18. A method as defined in claim 7 wherein the interpolation is performed by using read-outs of neighboring leads within a preset radius around the faulty lead.

19. A method as defined in claim 17 wherein said preset radius is twice the distance between electrodes.

20. A method as defined in claim 1 wherein said plurality of electrodes comprises between 24 and 128 electrodes;
said electrodes being distributed over the front, sides and back of the torso.

21. A method as defined in claim 20 wherein said read-outs from said electrodes are amplified, filtered, digitized and stored on a magnetic disc.

* * * * *